United States Patent [19]

Naumann et al.

[11] 4,076,517
[45] Feb. 28, 1978

[54] METHOD OF INHIBITING THE GROWTH OF PLANTS WITH PHOSPHOLENIUM SALTS

[75] Inventors: Klaus Naumann, Cologne; Klaus Sasse, Gladbach-Schildgen; Klaus Lurssen, Berg.-Gladbach, all of Germany

[73] Assignee: Bayer Aktiengesellschaft, Leverkusen, Germany

[21] Appl. No.: 649,439

[22] Filed: Jan. 15, 1976

[30] Foreign Application Priority Data

Jan. 27, 1975 Germany .............................. 2503210

[51] Int. Cl.² ................................................ A01N 9/36
[52] U.S. Cl. ............................................ 71/86; 71/76; 71/87
[58] Field of Search ........................... 71/86, 87, 76

[56] References Cited

U.S. PATENT DOCUMENTS

| 3,142,685 | 7/1964 | Backler et al. ............ 71/87 X |
| 3,414,624 | 12/1968 | Peterson et al. ........... 71/86 X |
| 3,531,514 | 9/1970 | Redmore ..................... 71/86 X |

OTHER PUBLICATIONS

Bond, et al.; J. Chem. Soc. (B), 1968, pp. 929–931.
Quin, et al.; J. Org. Chem.; 38, pp. 1954–1955 (1973).
Quin, et al.; Tetrahedron Letters; 1964, pp. 3689–3693.

*Primary Examiner*—Joseph Paul Brust
*Attorney, Agent, or Firm*—Burgess, Dinklage & Sprung

[57] ABSTRACT

Plant growth is regulated, e.g., inhibited, by applying to a plant or its habitat a composition containing as an active ingredient a phospholenium salt of the formula

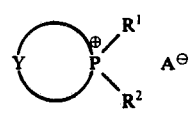

(I), in which
$R^1$ is alkyl, substituted alkyl, alkenyl, alkynyl, cycloalkyl, aralkyl, aralkyl substituted in the aryl part, alkoxy, substituted alkoxy, alkylthio or substituted alkylthio,
$R^2$ is alkyl, substituted alkyl, alkenyl, alkynyl, cycloalkyl, aralkyl or aralkyl substituted in the aryl part,
Y is a chain of the structure —$CH_2$—CH=CH—$CH_2$— or CH=CH—$CH_2$—$CH_2$— which can be substituted by at least one of halogen and alkyl, and
$A^-$ is one equivalent of an anion of a non-phytotoxic acid, in admixture with a solid or liquefied gaseous diluent or carrier or in admixture with a liquid diluent or carrier containing a surface-active agent.

5 Claims, No Drawings

METHOD OF INHIBITING THE GROWTH OF PLANTS WITH PHOSPHOLENIUM SALTS

The present invention relates to compositions for regulating plant growth containing certain phospholenium salts, and to methods of regulating plant growth utilizing such salts.

It is known that certain 2-halogen-ethanephosphonic acids exhibit plant-growth-regulating properties (see published Netherlands Patent Application No. 6,802,633). Thus, for example, it is possible to influence plant growth, and in particular inhibit vegetative plant growth in cereals and other crop plants, by applying 2-chloroethane-phosphonic acid thereto. However, the action of this compound is not always entirely satisfactory, especially if low amounts and low concentrations are used.

It has now been found that the phospholenium salts of the general formula

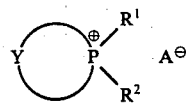
(I), in which
R$^1$ is optionally substituted alkyl, alkenyl, alkynyl or cycloalkyl, aralkyl which is optionally substituted on the aryl part, optionally substituted alkoxy or optionally substituted alkylthio,
R$^2$ is optionally substituted alkyl, alkenyl, alkynyl or cycloalkyl or aralkyl which is optionally substituted in the aryl part,
Y is a chain of the structure —CH$_2$-CH=CH-CH$_2$— or —CH=CH-CH$_2$-CH$_2$— which is optionally monosubstituted or disubstituted by halogen and-/or alkyl, and
A$^{31}$ is one equivalent of an anion of a non-phytotoxic acid,
exhibit powerful plant growth-regulating properties.

Surprisingly, the phospholenium salts according to the invention exhibit a substantially greater plant growth-regulating action than 2-chloroethane-phosphonic acid, known by the art to be a compound, of good activity having the same type of action. The compounds which can be used according to the invention thus represent a valuable enrichment of the art.

The present invention thus provides a plant-growth regulating composition containing as active ingredient a compound of the formula (I) in admixture with a solid or liquefied gaseous diluent or carrier or in admixture with a liquid or carrier containing a surface-active agent.

The present invention also provides a method of regulating the growth of plants, which comprises applying to the plants or a plant habitat a compound of the formula (I) alone or in the form of a composition containing as active ingredient a compound of the formula (I) in admixture with a diluent or carrier.

Preferably, in the formula (I), R$^1$ is straight-chain or branched alkyl with 1 to 4 carbon atoms (which alkyl can carry one or more substituents selected independently from hydroxyl, methoxy, methylcarbonyl, alkoxycarbonyl with 1 to 4 carbon atoms in the alkoxy group and halogen, especially chlorine and bromine), alkenyl with 2 to 4 carbon atoms, cycloalkyl with 3 to 12 carbon atoms, especially with 3 to 7 carbon atoms, aralkyl with 1 to 4 carbon atoms in the alkyl part and 6 to 10 carbon atoms in the aryl part (which aryl part is optionally substituted by halogen, for example chlorine), or alkoxy or alkylthio each with 1 to 4 carbon atoms; R$^2$ is straight-chain or branched alkyl with 1 to 4 carbon atoms (which alkyl can carry one or more substituents selected independently from hydroxyl, methoxy, methylcarbonyl, alkoxycarbonyl with 1 to 4 carbon atoms in the alkoxy group, and halogen, especially chlorine and bromine), alkenyl with 2 to 4 carbon atoms, alkynyl with 2 to 4 carbon atoms, cycloalkyl with 3 to 12 carbon atoms, especially with 3 to 7 carbon atoms, or aralkyl with 1 to 4 carbon atoms in the alkyl part and 6 to 10 carbon atoms in the aryl part (which alkyl part is optionally substituted by halogen, for example, chlorine); Y is a chain of the structure —CH$_2$-CH=CH-CH$_2$— or —CH=CH-CH$_2$-CH$_2$— which is optionally monosubstituted or disubstituted by chlorine, bromine or alkyl with 1 to 4 carbon atoms; and A$^-$ is alkyl-sulfate, especially methyl-sulfate or ethyl-sulfate, or halide.

The following may be mentioned as examples of the active compounds which can be used according to the invention; 1,1-dimethyl-phosphol-3-enium chloride, 1,1-dimethylphosphol-3-enium methosulfate, 1,1-diethylphosphol-3-enium bromide, 1-methyl-1-ethylphosphol-3-enium bromide, 1-methyl-1-benzylphosphol-3-enium chloride, 1-methyl-1-(2-hydroxyethyl)-phosphol-3-enium chloride, 1-methyl-1-(2-chloroethyl)-phosphol-3-enium chloride, 1-methyl-1-ethoxycarbonyl-methyl-phosphol-3-enium chloride, 1,1,2-trimethylphosphol-3-enium chloride, 1,1,3-triethylphosphol-3-enium chloride, 1,1-dimethyl-3,4-dichlorophosphol-3-enium chloride, 1-methyl-1-methoxy-phosphol-3-enium methosulfate, 1-methyl-1-methylmercapto-phosphol-3-enium slufate, 1-methyl-1-methoxy-phosphol-3-enium iodide, 1,1-dimethyl-phosphol-2-enium chloride, 1,1-dimethyl-phosphol-2-enium methosulfate, 1,1-diethylphosphol-2-enium bromide, 1-methyl-1-ethylphosphol-2-enium bromide, 1-methyl-1-benzylphosphol-2-enium chloride, 1-methyl-1-(2-hydroxyethyl)-phosphol-2-enium chloride, 1-methyl-1-(2-chloroethyl)-phosphol-2-enium chloride, 1-methyl-1-ethoxycarbonyl-methyl-phosphol-2-enium chloride, 1,1,2-trimethylphosphol-2-enium chloride, 1,1,3-trimethyl-phosphol-2-enium chloride, 1,1-dimethyl-3,4-dichlorophosphol-2-enium chloride, 1-methyl-1-methoxyphosphol-2-enium methosulfate and 1-methyl-1-methylmercaptophosphol-2-enium methosulfate.

Some of the compounds which can be used according to the invention are known (see J. Chem. Soc. (B) 1968, 929–31; Tetrahedron Letters 1964, 3689 and J. Org. Chem. 38, 1954–55 (1973)). However, their use as plant growth regulators has not been described in the prior art.

The compounds which can be used according to the invention and which are new can be prepared in a simple manner in accordance with known processes. For example, such a compound is obtained when a. a phosphol-3-ene of the general formula

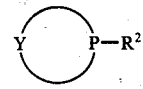
(II), in which

R² and Y have the above-mentioned meanings, is reacted with a compound of the general formula

R — X  (III), in which
R is optionally substituted alkyl, alkenyl, alkynyl or cycloalkyl, aralkyl which is optionally substituted in the aryl part, or the triethyl-oxonium ion, and
X is halogen, alkyl-sulfate or tetrafluoborate,
if appropriate in the presence of a solvent, at a temperature between 0° C and 130° C,
or when
b. a phospholanium salt of the general formula

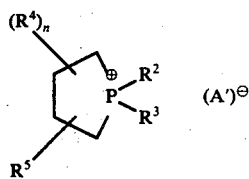

(IV), in which
R² has the above-mentioned meaning,
R³ is optionally substituted alkyl, alkenyl, alkynyl or cycloalkyl, or aralkyl which is optionally substituted in the aryl part,
R⁴ is halogen or alkyl,
R⁵ is halogen or an alkylsulfonyl or an arylsulfonyl radical,
n is 0, 1 or 2, and
(A')⁻ is a halide or alkyl-sulfate ion,
is reacted with a base, such as sodium hydroxide, or with an amine, at a temperature between 0° C and 100° C, if appropriate in the presence of a solvent, such as, for example, water, methanol or isopropanol, or when
c. a phospholene oxide or phospholene sulfide of the general formula (V), in which
R² and Y have the above-mentioned meanings and
Z is oxygen or sulfur,
is reacted with an alkylating agent, such as, for example, methyl iodide, dialkyl sulfate or trialkyloxonium tetrafluoborate, at a temperature between 0° C and 100° C, if appropriate in the presence of a solvent, such as dioxan or methanol.

The phospholenes of the formula (II) required as starting materials in carrying out the process variant (a) are known or can be prepared according to known processes (see Tetrahedron Letters 1964, 3689-3693).

The following may be mentioned as examples of phospholenes of the formula (II): 1-methylphosphol-3-ene, 1-methylphosphol-2-ene, 1-ethylphosphol-2-ene, 1-ethylphosphol-3-ene, 1-ethylphosphol-2-ene, 1,3-dimethylphosphol-3-ene, 1,3-dimethylphosphol-2-ene, 1,3,4-trimethylphosphol-3-ene and 1,3,4-trimethylphosphol-2-ene.

The compounds of the formula (III) which can also be used as starting materials in carrying out process variant (a), are also known. The following may be mentioned as examples: methyl iodide, methyl chloride, ethyl bromide, propyl chloride, allyl chloride, propargyl chloride, benzyl chloride, chloroacetone, chloroacetic acid or its esters, chloromethyl ether, chloromethylnaphthalene, dimethyl sulfate, diethyl sulfate and triethyloxonium tetrafluoborate.

Preferred solvents which can be used in carrying out process variant (a) are lower alcohols, such as, for example, methanol; hydrocarbons, such as toluene and cyclohexane; and strongly polar solvents, such as dimethylformamide, acetonitrile, acetone or water.

In carrying out process variant (a), preferably 1 mole of starting compound of the formula (III) is employed per mole of the phospholene of the formula (II). It is possible to deviate from the stoichiometric ratio, but this produces no significant improvement in yield.

In the preparation of the compounds which can be used according to the invention, in accordance with process variant (a), the reaction products are either directly obtained in a crystalline form after completion of the reaction or can be separated out in an oily state by adding a solvent in which they are insoluble. The crystalline products are isolated simply by filtration, if necessary after prior concentration of the reaction mixture. An additional purification by reprecipitating is possible. If the reaction products are obtained as oils, they are isolated by first separating the phases and then purifying the oil by treatment with active charcoal in aqueous or alcoholic solution.

The phospholanium salts of the formula (IV) required as starting material in carrying out process variant (b) are in some cases known; they can all be prepared according to known methods. A synthesis of the compounds of the formula (IV) which are not previously known from the literature can be effected by reacting a phospholane of the general formula

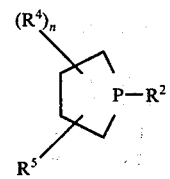

(VI), in which
R², R⁴, R⁵ and n have the above-mentioned meanings, with a compound of the general formula

R³ — X¹  (VII), in which
R³ has the above-mentioned meaning and
X¹ is halogen or alkyl-sulfate, if appropriate in the presence of a diluent, such as, for example, methanol, toluene, cyclohexane, dimethylformamide, acetonitrile, acetone or water, at a temperature between 0° C and 130° C. The phospholanes of the formula (VI) required as starting materials are known or can be prepared according to previously described processes (see J. Amer. Chem. Soc. 91, 4724–29 (1969). The compounds of the formula (VII), also required as starting materials, are also already known.

In carrying out process variant (b), preferably 1 equivalent of base is employed per mole of a phospholanium salt of the formula (IV).

When using process variant (b), the reaction products are isolated in accordance with customary methods. A suitable procedure is to concentrate the reaction mixture under reduced pressure after completion of the reaction, take up the residue in a suitable solvent which dissolves only the phospholenium salt, then treat the solution with active charcoal in order to purify it, and finally concentrate the solution, obtained after filtration, under reduced pressure.

The phospholene oxides and phospholene sulfides of the formula (V) which can be used as starting materials in carrying out process variant (c) are known or can be prepared according to previously described methods (see Synth. React. Inorg. Metalorg. Chem. 4 119-132 (1974) and Tetrahedron Letters 1964, 3689-93).

The following may be mentioned as examples of compounds of the formula (V): 1-methylphosphol-3-ene 1-oxide, 1-methylphosphol-2-ene 1-oxide, 1-methylphosphol-3-ene 1-sulfide and 1-methylphosphol-2-ene 1-sulfide.

In carrying out process variant (c), preferably 1 equivalent of an alkylating agent is employed per mole of phospholene oxide or phospholene sulfide of the formula (V). It is possible to deviate from the stoichiometric ratio but this produces no significant improvement in yield.

When using process variant (c), a suitable method of isolating the reaction products is to concentrate the reaction mixture, after completion of the reaction, and filter off the crystals which separate out. Additional purification by reprecipitation is possible. If the reaction products are obtained in the form of oils, they can be converted to the crystalline state by digestion with a polar solvent, such as, for example, acetone, and be obtained in a pure form after filtration.

In the compounds of the formula (I) which can be prepared in accordance with the above processes, the anion initially present can be replaced, in accordance with known methods, by other anions of non-phytotoxic acids. For example, the anion can be varied with the aid of charged anion exchangers.

The active compounds which can be used according to the invention engage in the metabolism of the plants and can therefore be employed as growth regulators.

Experience to date of the mode of action of plant growth regulators has shown that an active compound can exert one or several different types of action on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which again counteracts lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, whilst vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favorably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this for example, in the case of plant propagation by cuttings. However, it is also possible to inhibit the growth of side shoots, for example, to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit — for example in the case of table fruit — in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out completely mechanical or manual harvesting in only a single pass, for example in the case of tobacco, tomatoes or coffee.

By using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The active compounds to be used according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylene, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaoline, clays, talc, chalk, quartz, attapulgite, montmorillonite or diatomaceous earth, or ground cynthetic minerals, such as highly dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alklarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds to be used according to the invention can be present in the formulations as a mixture with other active compounds, such as fungicides, insecticides, acaricides and herbicides, and also as a mixture with fertilizers.

The formulations in general contain from 0.1 to 95 percent by weight of active compound, preferably from 0.5 to 90 percent by weight.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomizing, scattering, dusting, foaming, gassing and the like. Furthermore, it is possible to apply the active compounds in accordance with the ultra-low-volume (ULV) methods, to spread the active compound preparation or the active compound itself on plants or parts of plants or to inject the active compound preparation or the active compound itself into the soil. It is also possible to treat the seeds of plants.

The active-compound concentrations can be varied within a fairly wide range. In general, concentrations of 0.00005 to 2%, preferably of 0.0001 to 0.5%, by weight are used. Furthermore, in general 0.01 to 50 kg. preferably 0.05 to 10 kg. of active compound are employed per hectare of soil surface.

The preferred time of application of the growth regulators depends on the climatic and vegetative circumstances.

The present invention further provides means of yielding crop plants, the growth of which has been regulated by growing them in areas in which immediately prior to and/or during the time of the growing a compound of the formula (I) was applied alone or in admixture with a diluent or carrier. It will be seen that the usual methods of providing a harvested crop may be improved by the present invention.

The following examples illustrate, without limitation, the activity of the compounds according to the invention as growth regulators.

EXAMPLE A

Inhibition of growth/wheat
Solvent: 10 parts by weight of methanol
Emulsifier: 2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

Young wheat plants, in the 2-leave stage, were sprayed with the preparation of active compound until dripping wet. After the untreated control plants had grown to a height of about 60 cm, the additional growth was measured for all plants and the inhibition of growth was calculated in % of the additional growth of the control plants. 100% means that growth had stopped and 0% denotes a growth corresponding to that of the untreated control plants.

The active compounds, active compound concentrations and results can be seen from the table which follows:

Table A

| | Inhibition of growth/wheat | |
|---|---|---|
| Active compound | Active comp. concentration in % | Inhibition of growth in % |
| (control) | — | 0 |

Table A-continued

Inhibition of growth/wheat

| Active compound | | Active comp. concentration in % | Inhibition of growth in % |
|---|---|---|---|
| Cl—CH$_2$—CH$_2$—P(=O)(OH)—OH (known) | | 0.05 | 0 |
| (4) cyclohexenyl-P$^+$(CH$_3$)(CH$_3$) | CH$_3$SO$_4^{\ominus}$ | 0.025<br>0.050<br>0.100 | 15<br>30<br>40 |
| (5) cyclohexenyl-P$^+$(OCH$_3$)(CH$_3$) | CH$_3$SO$_4^{\ominus}$ | 0.05 | 8 |
| (6) cyclohexenyl-P$^+$(CH$_3$)(CH$_3$) | Cl$^{\ominus}$ | 0.025<br>0.050 | 25<br>40 |
| (3) cyclohexenyl-P$^+$(CH$_3$)(CH$_3$) | CH$_3$SO$_4^{\ominus}$ | 0.025<br>0.200 | 25<br>40 |
| (2) cyclohexenyl-P$^+$(SCH$_3$)(CH$_3$) | CH$_3$SO$_4^{\ominus}$ | 0.025<br>0.050<br>0.200 | 5<br>10<br>15 |

EXAMPLE B

Inhibition of growth/barley
Solvent: 10 parts by weight of methanol
Emulsifier: 2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

Young barley plants, in the 2-leave stage, were sprayed with the preparation of active compound until dripping wet. After the untreated control plants had grown to a height of about 60 cm, the additional growth was measured for all plants and the inhibition of growth was calculated in % of the additional growth of the control plants. 100% means that growth had stopped and 0% denotes a growth corresponding to that of the untreated control plants.

The active compounds, active compound concentrations and results can be seen from the table which follows:

Table B

Inhibition of growth/barley

| Active compound | | Active comp. concentration in % | Inhibition of growth in % |
|---|---|---|---|
| (control) | | — | 0 |
| Cl—CH$_2$—CH$_2$—P(=O)(OH)—OH (known) | | 0.050 | 0 |
| (3) cyclohexenyl-P$^+$(CH$_3$)(CH$_3$) | CH$_3$SO$_4^{\ominus}$ | 0.050 | 14 |
| (6) cyclohexenyl-P$^+$(CH$_3$)(CH$_3$) | Cl$^{\ominus}$ | 0.025<br>0.050<br>0.100 | 5<br>15<br>25 |
| (5) cyclohexenyl-P$^+$(OCH$_3$)(CH$_3$) | CH$_3$SO$_4^{\oplus}$ | 0.050 | 5 |
| (4) cyclohexenyl-P$^+$(CH$_3$)(CH$_3$) | CH$_3$SO$_4^{\oplus}$ | 0.050 | 15 |

EXAMPLE C

Inhibition of growth/soya beans
Solvent: 10 parts by weight of methanol
Emulsifier: 2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

Young soya bean plants, in the stage in which the first of the secondary leaves had unfolded, were sprayed with the preparations of active compound until dripping wet. After 2 weeks, the additional growth was measured and the inhibition of growth in % of the additional growth of the control plants was calculated. 100% means that growth had stopped and 0% denotes a growth corresponding to that of the untreated control plants.

The active compounds, active-compound concentrations and results can be seen from the table which follows.

Table C

Inhibition of growth/soya beans

| Active compound | Active compound concentration in % | Inhibition of growth in % |
|---|---|---|
| (control) | — | 0 |
| (6) cyclohexenyl-P$^+$(CH$_3$)(CH$_3$) Cl$^{\ominus}$ | 0.05 | 25 |

The preparation of the compounds of the formula (I) is illustrated by the following Examples.

EXAMPLE 1

Preparation of 1-methyl-1-methoxy-phosphol-3-enium iodide

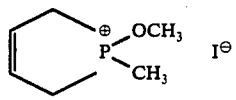 (1)

70.5 g (0.5 mole) of methyl iodide were added dropwise, whilst stirring, to a solution of 58 g (0.5 mole) of 1-methylphosphol-3-ene 1-oxide in 150 ml of ethyl acetate at room temperature. Thereafter the reaction mixture was left to stand for one hour at room temperature, and the crystalline precipitate which had separated out was then filtered off. The crystals were purified by washing them repeatedly with ethyl acetate. This gave 1-methyl-1-methoxy-phosphol-3-enium iodide as colorless crystals which on heating shift at between 70° C and 85° C.

Analysis: ($C_6H_{12}OPI$); Calculated: 11.9%, P; 49.6%, I; Found: 12.0%, P; 49.2%, I.

EXAMPLE 2

Preparation of 1-methyl-1-methyl-mercapto-phosphol-2-enium methosulfate

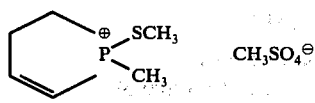 (2)

63 g (10.5 mole) of dimethyl sulfate were added dropwise, whilst stirring, to a solution of 66 g (0.5 mole) of 1-methyl-phosphol-2-ene 1-sulfide in 500 ml of dioxan at room temperature. The reaction mixture was then left to stand briefly at room temperature, after which the oil which separated out was separated off. The oil was purified by washing it repeatedly with acetone. This gave 1-methyl-1-methyl-mercapto-phosphol-2-enium methosulfate in the form of a colorless oil.

Analysis ($C_7H_{15}O_4S_2$): Calculated: 34.1%, C; 6.1%, H; 25.9%, S; Found 33.7%, C; 6.1%, H; 24.9%, S.

EXAMPLE 3

Preparation of 1,1-dimethyl-phosphol-3-enium methosulfate

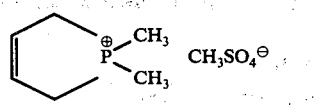 (3)

A mixture of 23 g (0.2 mole) of 1-methyl-phosphol-3-ene 1-oxide and 16.5 g (9.15 moles) of phenylsilane was carefully warmed under nitrogen atmosphere, until the exothermic reaction had ceased. The 1-methyl-phosphol-3-ene thereby produced was distilled directly from the reaction mixture into a receiver containing toluene and 25 g (0.2 mole) of dimethyl sulfate. The reaction mixture was left to stand for 10 hours at room temperature and the crystalline precipitate which had separated out was then filtered off. 32.4 g (72% of theory) of 1,1-dimethyl-phosphol-3-enium methosulfate were thus obtained in the form of colorless crystals of melting point 84°–88° C.

Analysis: ($C_7H_{15}O_4SP$); Calculated: 36.2%, C; 6.6%, H; 13.7%, P; 14.2%, S; Found: 36.2%, C; 6.4%, H; 13.8%, P; 14.5%, S.

EXAMPLE 4

Preparation of 1,1-dimethyl-phosphol-2-enium methosulfate

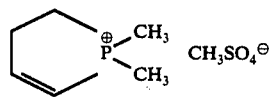 (4)

Following the method described in Example 3, 1-methylphosphol-2-ene 1-oxide was reacted with phenylsilane and the 1-methyl-phosphol-2-ene thereby produced was alkylated with dimethyl sulfate. This gave 1,1-dimethyl-phosphol-2-enium methosulfate in 70% yield, in the form of colorless crystals melting at between 95° C and 105° C.

Analysis ($C_7H_{15}O_4SP$); Calculated: 36.2%, C; 6.6%, H; 13.7%, P; 14.2%, S; Found: 36.5%, C; 6.6%, H; 13.8%, P; 14.4%, S.

EXAMPLE 5

Preparation of 1-methyl-1-methoxy-phosphol-3-enium methosulfate

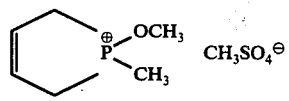 (5)

63 g (0.5 mole) of dimethyl sulfate were added dropwise, whilst stirring, to a solution of 58 g (0.5 mole) of 1-methyl-phosphol-3-ene oxide in 150 ml of ethyl acetate, at room temperature. The reaction mixture was then left to stand for one hour at room temperature and the oil which separated out was then separated off. The product was purified by washing it repeatedly with ethyl acetate. This gave 1-methyl-1-methoxy-phosphol-3-enium methosulfate in the form of a colorless viscous oil.

Analysis: ($C_7H_{15}O_5SP$); Calculated: 34.9%, C; 5.8%, H; 12.9%, P; 13.3%, S; Found: 35.2%, C; 5.8%, H; 13.5%, P; 13.5%, S.

EXAMPLE 6

Preparation of 1-1-dimethyl-phosphol-3-enium chloride

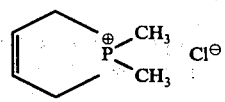 (6)

An aqueous solution of 1,1-dimethyl-phosphol-3-enium methosulfate was filtered through a column filled with an anion exchanger charged with chloride ions. After evaporating the eluate under reduced pressure, 1,1-dimethyl-phosphol-3-enium chloride was isolated in the form of colorless crystals.

It will be understood that the specification and examples are illustrative but not limitative of the present invention and that other embodiments within the spirit and scope of the invention will suggest themselves to those skilled in the art.

What is claimed is:

1. A method of inhibiting the growth of plants which comprises applying to the plants or a plant habitat an effective amount of a composition containing as active ingredient a phospholenium salt of the general formula

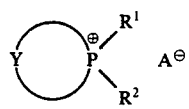 (I), in which

R$^1$ is alkyl of from 1 to 4 carbon atoms; substituted alkyl of from 1 to 4 carbon atoms wherein the substituents are selected from hydroxyl, methoxy, methylcarbonyl, alkoxycarbonyl with 1 to 4 carbon atoms in the alkoxy group and halogen; alkenyl of from 2 to 4 carbon atoms, cycloalkyl of from 3 to 12 carbon atoms, aralkyl of from 1 to 4 carbon atoms in the alkyl part and 6 to 10 carbon atoms in the aryl part, or aralkyl of from 1 to 4 carbon atoms in the alkyl part and 6 to 10 carbon atoms in the aryl part substituted in the aryl moiety by halogen; alkoxy and alkylthio of from 1 to 4 carbon atoms;

R$^2$ is alkyl of from 1 to 4 carbon atoms, substituted alkyl of from 1 to 4 carbon atoms wherein the substituents are selected from hydroxyl, methoxy, methylcarbonyl, alkoxycarbonyl with 1 to 4 carbon atoms in the alkoxy group, and halogen, alkenyl of from 2 to 4 carbon atoms, alkynyl of from 2 to 4 carbon atoms, cycloalkyl of from 3 to 12 carbon atoms, or aralkyl of from 1 to 4 carbon atoms in the alkyl part and 6 to 10 carbon atoms in the aryl part;

Y is a chain of the structure

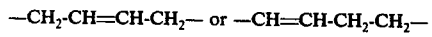

which can be monosubstituted or disubstituted by chlorine, bromine or alkyl of up to 4 carbon atoms, and A$^-$ is one equivalent of an anion of a non-phytotoxic acid.

2. A method as claimed in claim 1 wherein a composition is used containing from 0.00005 to 2% of the active compound, by weight.

3. A method as claimed in claim 2 wherein a composition is used containing from 0.0001 to 0.5% of the active compound is used.

4. A method as claimed in claim 1 wherein the active compound is applied to an area of plant cultivation in an amount of 0.01 to 50 kg per hectare.

5. A method as claimed in claim 4 wherein the active ingredient is applied in an amount of 0.05 to 10 kg per hectare.

* * * * *